(12) United States Patent
Bai et al.

(10) Patent No.: US 10,039,721 B2
(45) Date of Patent: Aug. 7, 2018

(54) DRESSING FOR PROMOTION OF WOUND HEALING

(71) Applicant: Life Star International Limited, New Taipei (TW)

(72) Inventors: Meng-Yi Bai, New Territories (HK); Meng-Chuan Chen, New Territories (HK); Wen-Chun Yu, New Territories (HK)

(73) Assignee: LIFE STAR INTERNATIONAL LIMITED, New Taipei (TW)

( * ) Notice: Subject to any disclaimer, the term of this patent is extended or adjusted under 35 U.S.C. 154(b) by 51 days.

(21) Appl. No.: 15/052,916

(22) Filed: Feb. 25, 2016

(65) Prior Publication Data

US 2017/0105943 A1 Apr. 20, 2017

(30) Foreign Application Priority Data

Oct. 16, 2015 (TW) .............................. 104134031 A

(51) Int. Cl.
| | |
|---|---|
| *A61K 38/17* | (2006.01) |
| *A61K 36/8988* | (2006.01) |
| *A61K 9/70* | (2006.01) |
| *A61L 15/40* | (2006.01) |
| *A61L 15/44* | (2006.01) |
| *A61L 26/00* | (2006.01) |
| *A61K 31/7034* | (2006.01) |
| *A61K 31/704* | (2006.01) |

(52) U.S. Cl.
CPC .......... *A61K 9/7007* (2013.01); *A61K 31/704* (2013.01); *A61K 31/7034* (2013.01); *A61K 36/8988* (2013.01); *A61K 38/1767* (2013.01); *A61L 15/40* (2013.01); *A61L 15/44* (2013.01); *A61L 26/0057* (2013.01); *A61L 26/0066* (2013.01); *A61L 2300/232* (2013.01)

(58) Field of Classification Search
None
See application file for complete search history.

(56) References Cited

U.S. PATENT DOCUMENTS

2014/0222152 A1* 8/2014 Kaplan .................. A61F 2/442
623/17.16

FOREIGN PATENT DOCUMENTS

WO    WO 2013071123 A1 * 5/2013 ........... A61L 27/227

OTHER PUBLICATIONS

Abdelaziz et al., "Antimicrobial and immunomodulation activities of hesperidin and ellagic acid against diarrheic Aeromonas hydrophilia in a murine model", Life Sciences, 2013, pp. 714-722.*
Kumar et al., "Gastrodin Protects Apoptotic Dopaminergic Neurons in a Toxin-Induced Parkinson's Disease Model", Evidence-Based Complementary and Alternative Medicine, 2013, pp. 1-13.*
Meng-Yi Bai et al., Evaluation of silk fibroin protein/poly(vinyl alcohol) transparent membranes as prospective patch for acne care, Journal of Bioactive and Compatible Polymers, 2015, vol. 30(5), 490-508.

* cited by examiner

*Primary Examiner* — Lianko G Garyu
(74) *Attorney, Agent, or Firm* — Anova Law Group, PLLC

(57) ABSTRACT

A dressing includes a silk protein layer and a hydrophilic glycoside compound, and the hydrophilic glycoside compound is coated on the silk protein layer. Furthermore, the invention also provides the use of a wound dressing comprising a silk protein layer and an active ingredient comprising a water extract of *Gastrodia elata* Blume, wherein the water extract containing gastrodin in a range from 0.33% to 0.67%.

3 Claims, 7 Drawing Sheets ic earth metal salt solution, the salt solution is heated to a temperature of 50 to 80° C., preferably 60 to 70° C. When the temperature of the salt solution reaches the temperature range described above, the silk protein is added into the salt solution, and the heating is continued to completely dissolve the silk protein, and thus obtaining a silk protein solution.

DRESSING FOR PROMOTION OF WOUND HEALING

CROSS REFERENCE

The non-provisional application claims priority from Taiwan Patent Application NO. 104134031, filed on Oct. 16, 2015, the content thereof is incorporated by reference herein.

BACKGROUND OF THE INVENTION

Field of the Invention

The present invention relates to technology field of wound dressings, and more particularly to a dressing for promotion of wound healing.

Description of the Prior Art

Skin, the largest organ of human body, acts as the first line of defense against foreign pathogens. Once the skin is wounded severely or in a large area, it might lose the ability of self-repair such that the wound is difficult to recover. Therefore, people may use the wound dressing to assist in wound healing. The wound dressing keeps the wound in a well hermetic and humid environment for epithelialization and new epithelial cell migration to occur.

Good wound dressings generally have properties, such as good water absorption, mechanical strength and biocompatibility. A commercially available wound dressing, also known as "artificial skin", is consisting essentially of: the bulk glue and the water-absorbing material. The bulk glue provides the dressing adhesion and strength to facilitate operation, such as rubber, gelatin and the like; and the water-absorbing material is mostly water-absorbing synthetic polymers, such as carboxymethyl cellulose, polyurethanes and the like. Since the commercially available wound dressings are difficult to decompose and likely to cause environmental pollution after use, there has been researches seeking to use natural alternatives.

SUMMARY OF THE INVENTION

The present invention is completed according to an unexpected discovery. This discovery combines the silk protein with the hydrophilic glycoside compound to promote wound healing, and the resultant healing efficacy is much better than that achieved by the silk protein alone or the hydrophilic glycoside compound alone.

Thus, one object of the present invention is to provide a novel dressing for promotion of wound healing, comprising:

a silk protein layer, being a freeze-dried product of a mixture obtained by mixing a dialysate containing silk protein and an ethanol solution, and having a plurality of pores with a porosity in a range between 17.2% and 32.8%; and an active ingredient, being infiltrated in the pores of the silk protein layer; wherein the active ingredient is a water extract of *Gastrodia elata* Blume containing gastrodin in a range from 0.33% to 0.67%.

DETAILED DESCRIPTION OF THE EMBODIMENTS

To make the above and/or other objects, efficacy, and features of the present invention more apparent, preferred embodiments will be set forth in the detailed description below:

One embodiment of the present invention provides a dressing, which comprises a silk protein layer, and a hydrophilic glycoside compound coating on the silk protein layer. The dressing provided by the present embodiment can promote wound healing, and thus can serve as a wound dressing. As used herein, the term "wound" can refer to a diabetic wound, a burn wound, a cut wound, or a surgical wound, but is not limited thereto. When the composition of the present embodiment is applied on the wound, the permeability of the dressing and absorption of wound exudates are enhanced to keep the wound in an environment of suitable humidity and thus promoting the healing efficacy. The silk protein layer may have a foam-like appearance. When the silk protein layer has a foam-like appearance, the porosity thereof is preferably between 15 to 35%. In addition, the example of the hydrophilic glycoside compound may be but not limited to gastrodin or hesperidin, and the source of such compound may be but not limited to the water extract of *Gastrodia elata* blume or seasoned orange peels. Furthermore, when the source is the water extract of *Gastrodia elata* blume, the gastrodin accounts for 0.33 to 0.67%, based on the weight of the water extract of *Gastrodia elata* blume; and when the source is the water extract of seasoned orange peels, the hesperidin accounts for 1.5 to 2.6%, based on the weight of the water extract of seasoned orange peels.

Figure 1:
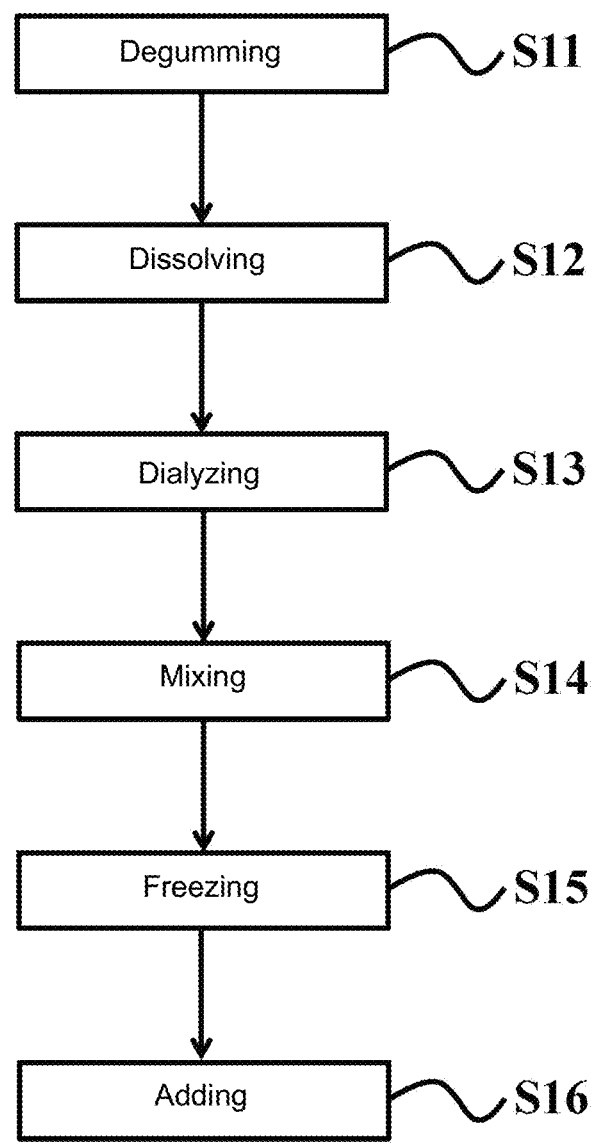
FIG. 1 is a flow diagram illustrating the method for manufacturing the composition in the embodiment of the present invention.

Referring to FIG. 1, the method for manufacturing the dressing of the embodiment described above includes the following steps: degumming step (S11), dissolving step (S12), dialyzing step (S13), mixing step (S14), freezing step (S15), and adding step (S16).

The degumming step (S11) degums the cocoon to obtain the silk protein. When carrying out this step, the cocoon can be put into the deionized water, and the resulting mixture is sterilized in a high temperature autoclave; the liquid in the sterilized mixture is then removed to obtain the crude extract of the silk protein; and finally, the crude extract of the silk protein is washed and dried to obtain the silk protein. In this embodiment, the weight ratio of the cocoon to the deionized water ranges from about 1:40 to 1:60, and is preferably 1:50.

The dissolving step (S12) dissolves the silk protein in the alkali metal or alkaline earth metal salt solution. To assist the silk protein in dissolving into the alkali metal or alkaline earth metal salt solution, this step can be carried out at 50 to 60° C. Moreover, the example of the alkali metal salt solution may be but not limited to the alkali metal halide solution, such as lithium bromide solution; and the example of the alkaline earth metal salt solution may be but not limited to the alkaline earth metal halide solution.

The dialyzing step (S13) dialyzes the alkali metal or alkaline earth metal salt solution dissolving the silk protein to obtain the dialysate containing the silk protein. During this step, the alkali metal or alkaline earth metal salt solution may be poured into the dialyzing membrane having pores, the size of which is smaller than the size of the silk protein, and then the dialyzing membrane is put into the deionized water. To enhance the dialyzing performance, it's preferred to carry out this step for four days, during which the deionized water is replaced every one hour for the first day and every eight hours for the second to fourth days.

The mixing step (S14) mixes the dialysate containing the silk protein with the ethanol solution to obtain a mixture. The example of the ethanol solution may be but not limited to 15 to 30% ethanol solution. In addition, for the mixture, the volumetric ratio of the dialysate to the ethanol solution ranges from about 1:0.5 to 1:2, and is preferably 1:1.

The freezing step (S15) freezes the mixture at −20 to −196° C. to obtain the silk protein layer.

The adding step (S16) adds the hydrophilic glycoside compound to the silk protein layer to obtain the dressing of the present embodiment. During this step, the silk protein layer may be immersed in the solution containing the hydrophilic glycoside compound; or the solution containing the hydrophilic glycoside compound may be sprayed on the silk protein layer.

The following embodiments are exemplified herein to illustrate the present invention:

Preparation Embodiment 1

Added 10 g of treated cocoons to the beaker containing 500 ml of deionized water, and covered the beaker with aluminum foil. After the beaker was sterilized in the autoclave, the liquid in the beaker was removed, leaving the crude extract of the silk protein in the beaker. Next, the crude extract of the silk protein was placed in the test sieve, washed by deionized water, and pressed out the water to obtain the silk protein. Then, the silk protein was dried.

Next, added 5 g of dried silk protein to the beaker containing 50 ml of 9 M lithium bromide solution. The beaker was heated up to 50 to 60° C. and held for a period of time until the lithium bromide solution became pale yellow and sticky, which represented the silk protein had been dissolved in the lithium bromide solution.

Afterwards, the lithium bromide solution dissolving the silk protein was poured into the 3.5 kD dialysis membrane. A clip was used to close the open end of the dialysis membrane for the solution to be poured in, and then the dialysis membrane was placed in the beaker containing deionized water, which was then rotated by a magnet for four days. The deionized water was replaced every one hour for the first day and every eight hours for the second to the fourth days.

Figure 2:
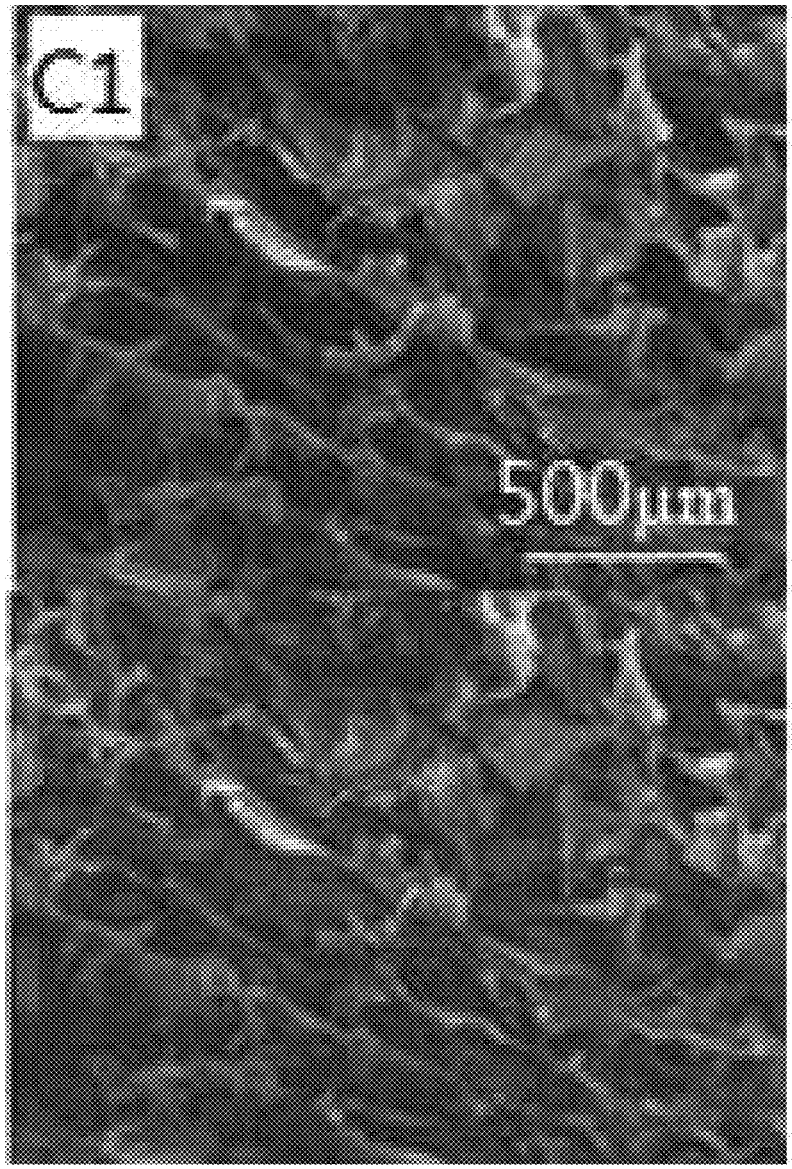
FIG. 2 is a scanning electron microscope image showing the porosity of the silk protein layer obtained in Preparation Embodiment 1.

Finally, 30 ml of dialysate containing the silk protein was took out from the dialysis bag and then mixed with 30 ml of 15 to 30% ethanol solution. The resultant mixture was frozen at −20° C. to obtain the foam-like silk protein layer (as shown in FIG. 2).

The measured porosity of the silk protein layer obtained in this embodiment was approximately 17.2%.

Preparation Embodiment 2

Figure 3:
FIG. 3 is a photograph showing the silk protein layer obtained in Preparation Embodiment 2.
Figure 4:
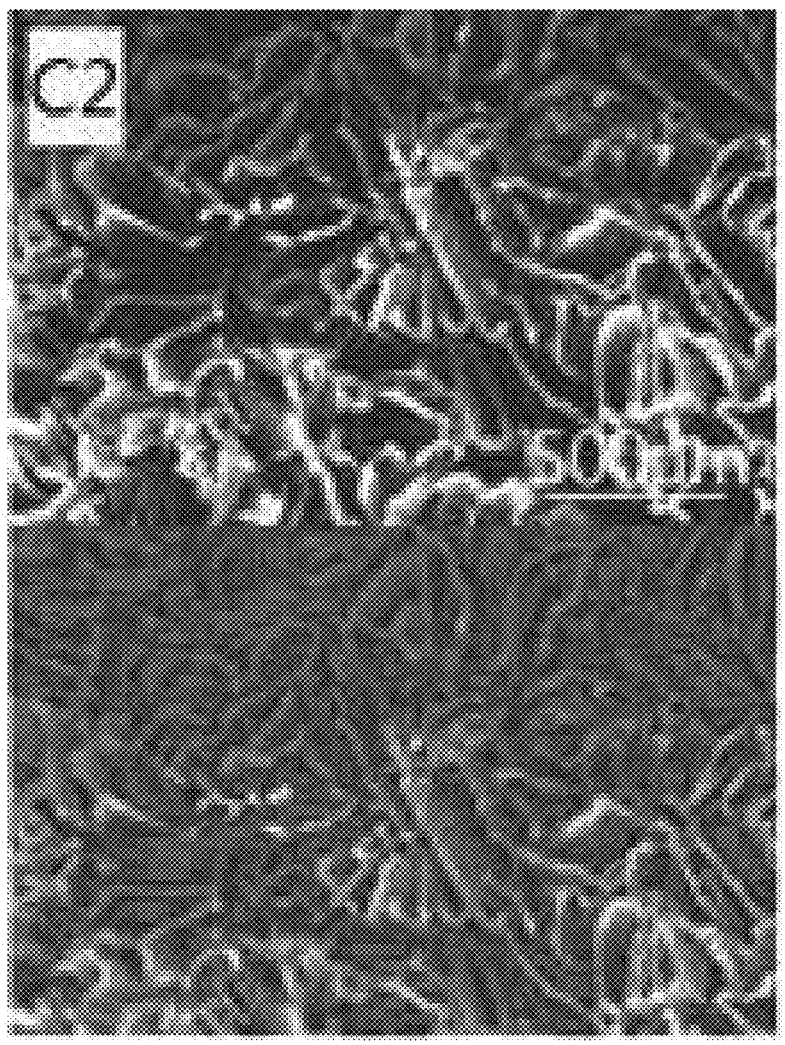
FIG. 4 is a scanning electron microscope image showing the porosity of the silk protein layer obtained in Preparation Embodiment 2.

The foam-like silk protein layer (as shown in FIGS. 3 and 4) obtained in this preparation embodiment was made following the process shown in Preparation Embodiment 1, except that the freezing temperature was −80° C.

The measured porosity of the silk protein layer obtained in this embodiment was approximately 32.8%.

Preparation Embodiment 3

Figure 5:
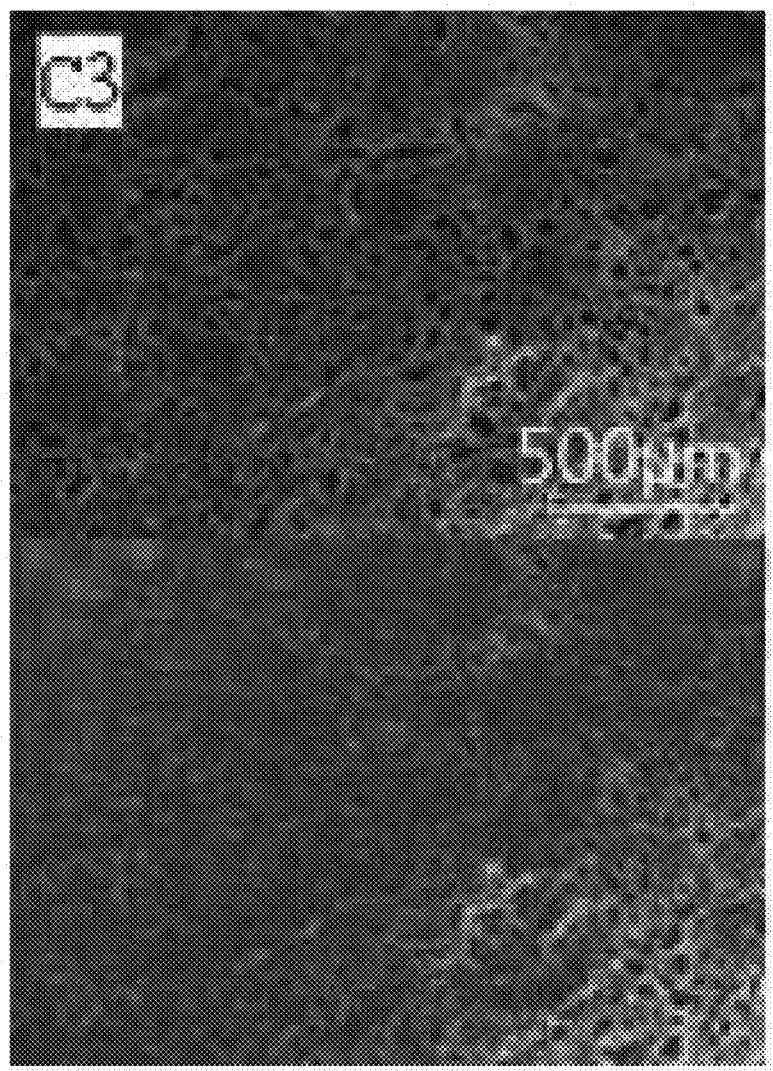
FIG. 5 is a scanning electron microscope image showing the porosity of the silk protein layer obtained in Preparation Embodiment 3.

The foam-like silk protein layer (as shown in FIG. 5) obtained in this preparation embodiment was made following the process shown in Preparation Embodiment 1, except that the freezing temperature was −196° C.

The measured porosity of the silk protein layer obtained in this embodiment was approximately 26.4%.

Preparation Embodiment 4

The silk protein layers obtained in Preparation Embodiment 2 were immersed in the low concentration water extract of *Gastrodia elata* blume (containing about 0.33% of gastrodin) and high concentration water extract of *Gastrodia elata* blume (containing about 0.67% of gastrodin), respectively.

Analysis Embodiment

First, a wound was created on the back of each mouse for the diabetic model. Thereafter, different dressings were applied to these mice, respectively. Also, the area of the wound on the back of each mouse was measured before the application of the dressing and different days after the application.

Figure 6:
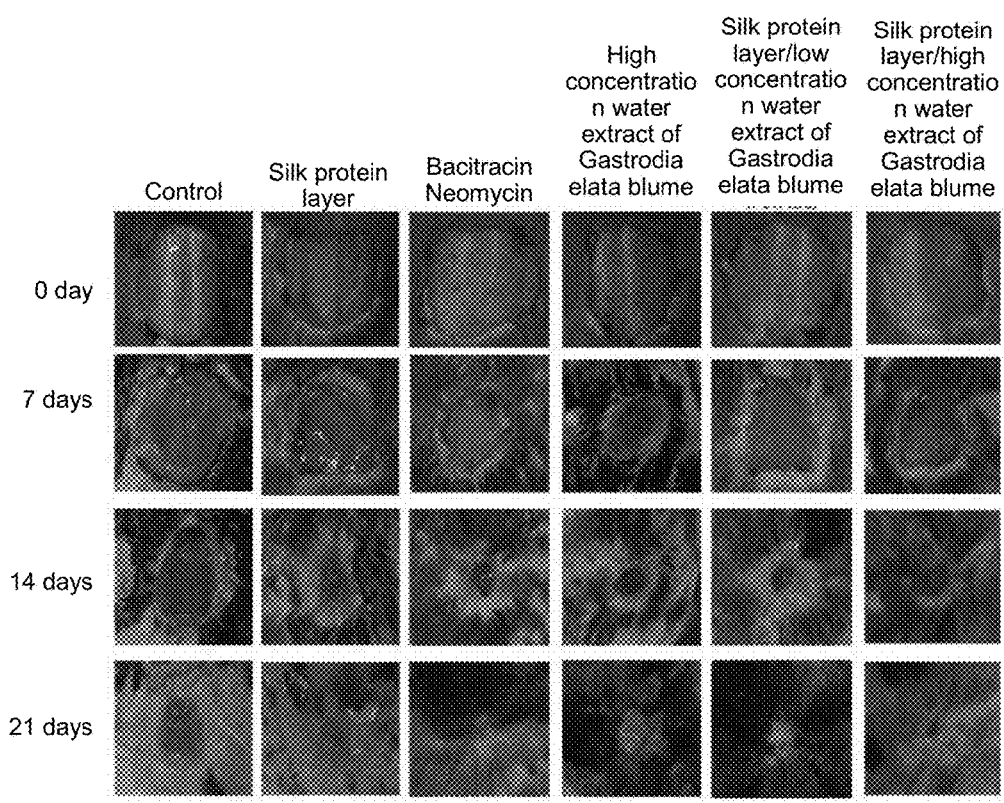
FIG. 6 is a photograph showing the healing efficacy of a wound on the back of a diabetic mouse treated by different dressings for different days.
Figure 7:
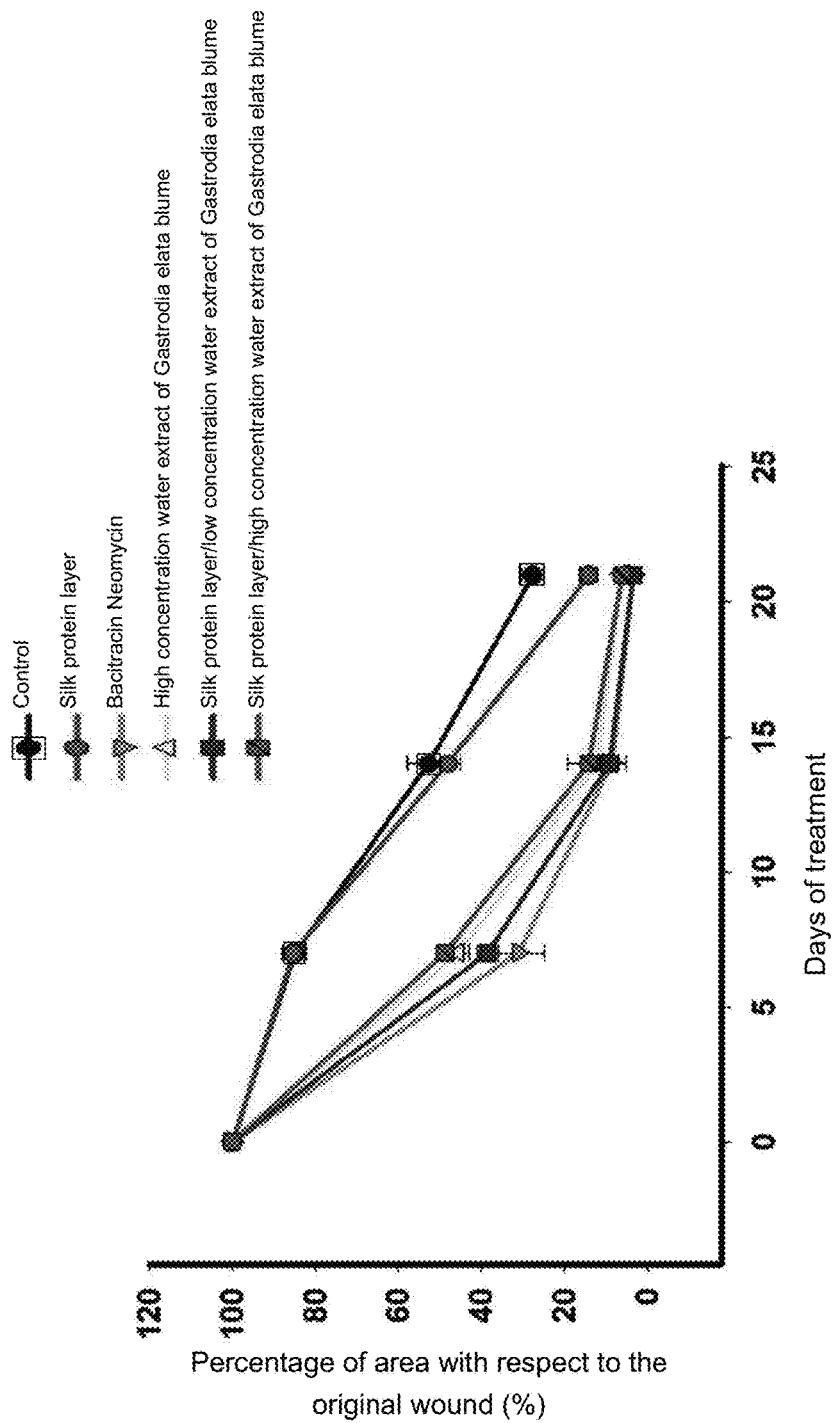
FIG. 7 is a graph showing the healing efficacy of a wound on the back of a diabetic mouse treated by different dressings for different days.

As shown in FIGS. 6 and 7, in the twenty-first day after the application, both the wounds on the backs of the mouse treated by the silk protein layer combined with the low concentration water extract of *Gastrodia elata* blume and the silk protein layer combined with the high concentration water extract of *Gastrodia elata* blume completely healed. By contrast, in the twenty-first day after the application, both the wounds on the backs of the mouse treated by the silk protein layer alone and the high concentration water extract of *Gastrodia elata* blume alone still had 10-18% not healed yet.

To sum up, it was confirmed that the dressing of the present invention can promote the healing of wounds, and the efficacy achieved thereof are much better than the efficacy achieved by the silk protein layer alone or the hydrophilic glycoside compound alone.

Those described above are only the preferred embodiments of the present invention, and cannot be used to limit the scope of the present invention; therefore, all the simple and equivalent variations and modifications made according to the claims and the specification of the present invention are within the scope of the present invention.

What is claimed is:

1. A dressing for promotion of wound healing, comprising:

a silk protein layer, being a freeze-dried product of a mixture obtained by mixing a dialysate containing silk protein and an ethanol solution and having a plurality of pores with a porosity in a range between 17.2% and 32.8%; and an active ingredient, being infiltrated in the pores of the silk protein layer;

wherein the active ingredient is a water extract of *Gastrodia elata* Blume containing gastrodin in a range from 0.33% to 0.67%.

2. A method for wound healing, comprising:

applying a wound dressing comprising the composition of claim 1 to a wound of a subject.

3. The method of claim 2, wherein the wound of the subject is a diabetic wound, a burn wound, a cut wound, or a surgical wound.

* * * * *